United States Patent
Cho et al.

(10) Patent No.: US 11,040,072 B2
(45) Date of Patent: *Jun. 22, 2021

(54) COMPOSITION FOR INDUCING BEIGE ADIPOCYTE DIFFERENTIATION CONTAINING EXOSOME DERIVED FROM STEM CELLS

(71) Applicant: EXOSTEMTECH CO., LTD., Ansan (KR)

(72) Inventors: Yong Woo Cho, Seongnam (KR); Ji Suk Choi, Gunpo (KR); Youn Jae Jung, Gunpo (KR); Woolee Cho, Busan (KR)

(73) Assignee: ExoStemTech Co., Ltd., Ansan (KR)

( * ) Notice: Subject to any disclaimer, the term of this patent is extended or adjusted under 35 U.S.C. 154(b) by 283 days.

This patent is subject to a terminal disclaimer.

(21) Appl. No.: 16/073,297

(22) PCT Filed: Jan. 2, 2017

(86) PCT No.: PCT/KR2017/000019
§ 371 (c)(1),
(2) Date: Jul. 26, 2018

(87) PCT Pub. No.: WO2017/131352
PCT Pub. Date: Aug. 3, 2017

(65) Prior Publication Data
US 2019/0030079 A1    Jan. 31, 2019

(30) Foreign Application Priority Data

Jan. 26, 2016  (KR) .................. 10-2016-0009513

(51) Int. Cl.
| | | |
|---|---|---|
| *A61K 35/35* | (2015.01) | |
| *A61K 35/48* | (2015.01) | |
| *C12N 5/077* | (2010.01) | |
| *A61K 35/28* | (2015.01) | |
| *A61K 35/51* | (2015.01) | |
| *A23L 33/10* | (2016.01) | |
| *A61P 3/04* | (2006.01) | |
| *A61P 3/10* | (2006.01) | |
| *C12N 5/0775* | (2010.01) | |

(52) U.S. Cl.
CPC .............. *A61K 35/28* (2013.01); *A23L 33/10* (2016.08); *A61K 35/35* (2013.01); *A61K 35/51* (2013.01); *A61P 3/04* (2018.01); *A61P 3/10* (2018.01); *C12N 5/0653* (2013.01); *C12N 5/0667* (2013.01); *C12N 2501/33* (2013.01); *C12N 2501/39* (2013.01); *C12N 2506/1353* (2013.01); *C12N 2506/1369* (2013.01); *C12N 2506/1384* (2013.01)

(58) Field of Classification Search
None
See application file for complete search history.

(56) References Cited

U.S. PATENT DOCUMENTS

| | | | | |
|---|---|---|---|---|
| 10,335,437 | B2 * | 7/2019 | Gillette | .................... A61P 3/04 |
| 2011/0117066 | A1 | 5/2011 | Ailhaud et al. | |
| 2017/0191035 | A1 * | 7/2017 | Sia | ........................ C12N 5/0653 |

FOREIGN PATENT DOCUMENTS

| | | |
|---|---|---|
| KR | 1020130116552 A | 10/2013 |
| KR | 1020140066456 A | 6/2014 |
| KR | 101572162 B1 | 11/2015 |
| WO | 2014026201 A1 | 2/2014 |
| WO | 2016007841 A1 | 1/2016 |

OTHER PUBLICATIONS

Baglio et al Human bone marrow- and adiposemesenchymal stem cells secrete exosomes enriched in distinctive miRNA and tRNA species Stem Cell Research & Therapy (2015) 6:127; pp. 1-20.*
waynesword.palomar.edu/trfeb98.htm; pp. 1-19; last visited Oct. 7, 2020.*
en.wikipedia.org/wiki/vertebrates, pp. 1-13; last visited Oct. 7, 2020.*
Sano et al Lipid synthesis is promoted by hypoxic adipocyte-derived exosomes in 3T3-L1 cells Biochemical and Biophysical Research Communications 445 (2014) 327-333.*
Yuan Zhang et al., "Irisin Stimulates Browning of White Adipocytes Through Mitogen Activated Protein Kinase p38 MAP Kinase and ERK MAP Kinase Signaling", Diabetes, Feb. 2014, pp. 514-525, vol. 63, American Diabetes Association.
International Search Report for PCT/KR2017/000019 dated Mar. 28, 2017.
JS Choi et al., "Exosomes from differentiating human skeletal muscle cells trigger myogenesis of stem cells and provide biochemical cues for skeletal muscle regeneration", Jan. 18, 2016, Elsevier, https://www.ncbi.nlm.nih.gov/pubmed/26699421.

* cited by examiner

Primary Examiner — Maria G Leavitt (57) ABSTRACT

The present disclosure relates to a composition for inducing differentiation into beige adipocytes, which contains an exosome derived from stem cells differentiating into beige adipocytes as an active ingredient, a pharmaceutical composition, a health functional food and a differentiation medium composition containing the composition and a method for inducing differentiation into beige adipocytes using the same.

11 Claims, 10 Drawing Sheets

Scale bars represent 200 μm

Scale bars represents 100nm

| Particle Concentration | 2.19 x 10¹⁰ particles/mL |
|---|---|
| Protein Concentration | 1.59 mg/mL |
| Purity | 1.37 x 10⁷ particles/µg |

FIG. 5

Scale bar represents 20 μm.

FIG. 6

Scale bars represent 100 µm.

COMPOSITION FOR INDUCING BEIGE ADIPOCYTE DIFFERENTIATION CONTAINING EXOSOME DERIVED FROM STEM CELLS

CROSS-REFERENCE TO RELATED APPLICATIONS

This application is a U.S. National Stage of International Patent Application No. PCT/KR2017/000019, filed on Jan. 2, 2017, which claims priority to Korean Patent Application No. 10-2016-0009513, filed on Jan. 26, 2016, which are hereby incorporated by reference in their entirety

TECHNICAL FIELD

The present disclosure relates to a composition for inducing differentiation into beige adipocytes, which contains an exosome derived from stem cells differentiating into beige adipocytes as an active ingredient, a pharmaceutical composition, health functional food and a differentiation medium composition containing the composition and a method for inducing differentiation into beige adipocytes using the same.

BACKGROUND ART

Adipocytes are largely classified into white adipocytes, brown adipocytes and beige adipocytes. White adipocytes mainly store energy in the form of triglycerides. When the white adipocytes increase excessively or do not function normally, obesity or other metabolism-related diseases may occur. Brown adipocytes consume energy by generating heat and prevent obesity. Beige adipocytes (or brite adipocytes) are mixed with white adipocytes and function similarly to the white adipocytes. However, when the beige adipocytes are activated with exercise, etc., they function similarly to the brown adipocytes. That is to say, because the beige adipocytes are rich in mitochondria unlike the white adipocytes, they generate heat in the body. The brown adipocytes which play beneficial roles in our bodies are mostly found in newborn infants. They are also present in adults but the quantity is relatively small. Therefore, there have been consistent efforts to increase the beige or brown adipocytes.

Formerly, chemicals or genetically recombinant proteins have been used to induce differentiation into beige adipocytes. For example, a culture medium containing the antidiabetic rosiglitazone or a beta-adrenergic agonist is generally used to induce differentiation of stem cells into beige adipocytes (U.S. Patent Publication No. 2011-0117066). These drugs are effective in differentiation into brown or beige adipocytes. However, they are difficult to handle because they do not dissolve well in water and are difficult to be applied to the body due to side effects related with cardiovascular diseases or neurological diseases.

In addition, although a method of promoting differentiation into brown adipocytes by suppressing the expression of the protein tyrosine phosphatase, receptor type E (PTP-RE) has been proposed, this method uses the genetic recombination technique and does not ensure safety when applied to the human body (Korean Publication Registration No. 1572162).

Bone morphogenetic proteins (BMP4 and BMP7) or the protein irisin are known to facilitate the activation of brown adipocytes in the body. Recently, it was reported that irisin present in the body convert white adipocytes into beige adipocytes (Yuan Zhang et al., 2014, *Diabetes*, 63: 514-525). Irisin is a protein produced in muscle in response to exercise and facilitate heat generation in the body by inducing the conversion of white adipocytes into beige adipocytes. However, because the commercially available irisin is produced through genetic recombination, there is a safety issue in application to the human body. That is to say, the genetically recombinant protein is difficult to be actually applied to the human body because safety is not ensured.

As described above, although the chemicals or genetically recombinant proteins that have been used formerly can induce differentiation into beige adipocytes, they may cause obesity, heart disease, etc. and are highly likely to cause various diseases when administered directly into the body because safety is not ensured.

Meanwhile, bionanoparticles secreted from various cells present in multicellular organisms including human can be classified into exosomes and microvesicles depending on their size and difference in secretion mechanism. Exosomes are membrane vesicles secreted from various types of cells and are known to play various roles such as transfer of membrane components, proteins and RNAs by binding to other cells and tissues.

DISCLOSURE

Technical Problem

The inventors of the present disclosure have researched on a method for inducing differentiation into beige adipocytes with superior safety in the body and have completed the present disclosure by identifying the effect of inducing differentiation into beige adipocytes of an exosome containing genetic information related with differentiation into beige adipocytes, proteins and growth factors.

Technical Solution

Accordingly, the present disclosure is directed to providing a composition for inducing differentiation into beige adipocytes, which contains an exosome derived from stem cells differentiating into beige adipocytes as an active ingredient.

The present disclosure is also directed to providing a pharmaceutical composition, a health functional food or a differentiation medium composition containing the composition.

The present disclosure is also directed to providing a method for inducing differentiation into beige adipocytes using the composition for inducing differentiation into beige adipocytes.

Advantageous Effects

An exosome according to a specific exemplary embodiment of the present disclosure has a superior effect of inducing differentiation of stem cells or white adipocytes into beige adipocytes. The exosome secreted during the process of differentiation of stem cells into beige adipocytes contains a large quantity of genes, proteins and growth factors associated with differentiation and, thus, has an excellent ability of inducing differentiation into beige adipocytes. In addition, it is safer in the body than existing differentiation-inducing agents and, thus, can effectively transfer differentiation-related factors into cells. Accordingly, it is expected that it can be applied as a therapeutic agent for obesity and diabetes in the future as a composition for inducing differentiation of stem cells into beige adipocytes and transdifferentiation of white adipocytes into beige adipocytes.

DESCRIPTION OF DRAWINGS

FIG. 3C: the expression of the protein of UCP1, the major differentiation factor of beige adipocytes, confirmed using an ELISA kit].

FIGS. 4A-4D shows the characteristics of an exosome derived from stem cells differentiating into beige adipocytes [FIG. 4A: the structure and morphology of the exosome (transmission electron microscopy), FIG. 4B: the size of the exosome (nanoparticle size analyzer, dynamic light scattering), FIG. 4C: exosomal membrane surface markers (western blot), FIG. 4D: the yield and purity of the isolated exosome (nanoparticle tracking analyzer, nanoparticle tracking analysis), BA: beige adipocytes, D-EXO: exosome derived from stem cells differentiating into beige adipocytes].

BEST MODE

The present disclosure provides a composition for inducing differentiation into beige adipocytes, which contains an exosome derived from stem cells differentiating into beige adipocytes as an active ingredient.

As used herein, the term "beige adipocytes (brite adipocytes)" refers to adipocytes of beige color, which normally function similarly to white adipocytes but can function similarly to brown adipocytes in response to specific stimulations such as exercise, etc. Unlike the white adipocytes, they are rich in mitochondria and generate heat in the body.

The "stem cells differentiating into beige adipocytes" refer to stem cells which are differentiating from beige adipose tissue-derived stem cells into beige adipocytes. From this, an exosome containing the genetic information, proteins and growth factors of the adipocytes can be isolated.

As used herein, the term "exosome" refers to a membrane vesicle secreted from various types of cells. It is known to play various roles such as transfer of membrane components, proteins and RNAs by binding to other cells and tissues.

The exosome may be isolated by an exosome extraction method known in the art.

The induction of differentiation into beige adipocytes may refer to induction of differentiation of stem cells into beige adipocytes or induction of transdifferentiation of white adipocytes into beige adipocytes.

The stem cells differentiating into beige adipocytes may be bone marrow stem cells, umbilical cord stem cells or adipose-derived stem cells.

The bone marrow stem cells, umbilical cord stem cells or adipose-derived stem cells may be human-, animal- or plant-derived stem cells.

The stem cells induced to differentiate into beige adipocytes may be adult stem cells.

The present disclosure also provides a pharmaceutical composition containing the composition for inducing differentiation into beige adipocytes.

The pharmaceutical composition may be for treating or preventing a metabolic disease.

The metabolic disease may be obesity or diabetes.

The pharmaceutical composition according to the present disclosure may be in the form of various oral or parenteral formulations. The formulation may be prepared using a commonly used diluent or excipient, such as a filler, an extender, a binder, a wetting agent, a disintegrant, a surfactant, etc. Solid formulations for oral administration include a tablet, a pill, a powder, a granule, a capsule, etc. Such solid formulations may be prepared by mixing at least one compound with at least one excipient, for example, starch, calcium carbonate, sucrose, lactose, gelatin, etc. In addition to simple excipients, a lubricant such as magnesium stearate, talc, etc. may also be used.

Liquid formulations for oral administration include a suspension, a liquid for internal use, an emulsion, a syrup, etc. In addition to commonly used simple diluents such as water and liquid paraffin, the liquid formulation may also contain various excipients, for example, a wetting agent, a sweetener, an aromatic, a preservative, etc.

Formulations for parenteral administration include a sterile aqueous solution, a non-aqueous solvent, a suspension, an emulsion, a freeze-dried formulation and a suppository.

As for the pharmaceutical composition according to the present disclosure, propylene glycol, polyethylene glycol, a vegetable oil such as olive oil, an injectable ester such as ethyl oleate, and the like may be used as the non-aqueous solvent and suspending agent. Witepsol, macrogol, tween 61, cacao butter, laurinum, glycerol gelatin and the like may be used as a suppository base.

The dosage form of the pharmaceutical composition according to the present disclosure may be in the form of a pharmaceutically acceptable thereof and it may be used alone or in suitable combination with other pharmaceutically active compounds. The salt of is not particularly limited as long as it is pharmaceutically acceptable. The salt includes, for example, the salt of hydrochloric acid, sulfuric acid, nitric acid, phosphoric acid, hydrofluoric acid, hydrobromic acid, formic acid, acetic acid, tartaric acid, lactic acid, citric acid, fumaric acid, malic acid, succinic acid, methanesulfonic acid, benzenesulfonic acid, toluenesulfonic acid, naphthalenesulfonic acid, etc.

The pharmaceutical composition according to the present disclosure may be parenterally or orally administered depending on the purpose, and may be administered once or multiple times a day as needed such that the amount administered is 0.1-500 mg or 1-100 mg per kg body weight. The administration dosage for a specific patient may vary depending on the patient's body weight, age, gender, health conditions and diet, the period of administration, the mode of administration, excretion rate, the severity of the disease, and the like.

According to a conventional method, the pharmaceutical composition according to the present disclosure may be used by formulating into any form suitable for a pharmaceutical formulation including oral formulations such as a powder, a granule, a tablet, a capsule, a suspension, an emulsion, a syrup, an aerosols, etc., external formulations such as an ointment, a cream, etc., a suppository, a sterilized injectable solution, and the like.

The pharmaceutical composition according to the present disclosure may be administered to a mammal such as rat, mouse, livestock, human, etc. through various routes such as parenteral and oral routes. Although all routes of administration can be expected, it may specifically be administered via oral, rectal, intravenous, intramuscular, subcutaneous, intrauterine, or intracerebroventricular routes.

The pharmaceutical composition according to the present disclosure may further contain a differentiation-inducing agent such as insulin, dexamethasone, dehydroepiandrosterone (DHEA), histamine, isobutylmethylxanthine, etc. in order to differentiate stem cells or white adipocytes into adipocytes, although not being limited thereto.

The present disclosure also provides a health functional food containing the composition for inducing differentiation into beige adipocytes.

The health functional food may be for improving or preventing a metabolic disease.

The metabolic disease may be obesity or diabetes.

The present disclosure also provides a medium composition for inducing differentiation into beige adipocytes, which contains the composition for inducing differentiation into beige adipocytes.

The medium composition for inducing differentiation into beige adipocytes may further contain a differentiation-inducing agent such as insulin, dexamethasone, dehydroepiandrosterone (DHEA), histamine, isobutylmethylxanthine, etc. in order to differentiate stem cells or white adipocytes into adipocytes, although not being limited thereto.

The present disclosure also provides a method for inducing differentiation of stem cells into beige adipocytes, which includes a step of treating stem cells with the composition for inducing differentiation into beige adipocytes.

The stem cells may be adult stem cells.

The present disclosure also provides a composition for inducing differentiation of stem cells into beige adipocytes and transdifferentiation of white adipocytes into beige adipocytes using an exosome derived from stem cells.

The method according to the present disclosure may include a step of isolating and purifying an exosome secreted during the process of differentiation of adult stem cells into beige adipocytes and a step of differentiating adult stem cells into beige adipocytes using the isolated exosome. The beige adipocytes function similarly to brown adipocytes. Unlike white adipocytes, they are rich in mitochondria and generate heat in the body. Because the exosome isolated according to the present disclosure contains various genetic information and growth factors which play important roles in differentiation into beige adipocytes, it can be effectively used for differentiation of stem cells into beige adipocytes and transdifferentiation of white adipocytes into beige adipocytes.

The exosome for inducing differentiation into beige adipocytes according to the present disclosure contains differentiation-related genetic information, proteins and growth factors. The exosome, which is composed of lipids of about 50 to 150 nm in size, is highly safe in the body because it is a cell-derived material, and shows an excellent cell absorption rate. Therefore, it is advantageous over the existing chemicals or genetically recombinant proteins in terms of effect and superior safety in the body.

MODE FOR DISCLOSURE

Hereinafter, embodiments of the present disclosure will be described in detail to help understanding of the present disclosure. However, various modifications and changes could be made to the embodiments of the present disclosure, and it should be understood that the scope of the disclosure is not limited to the following embodiments. The embodiments of the present disclosure are provided to persons having an ordinary skill in the art for more complete description of the present disclosure.

Figure 3A:
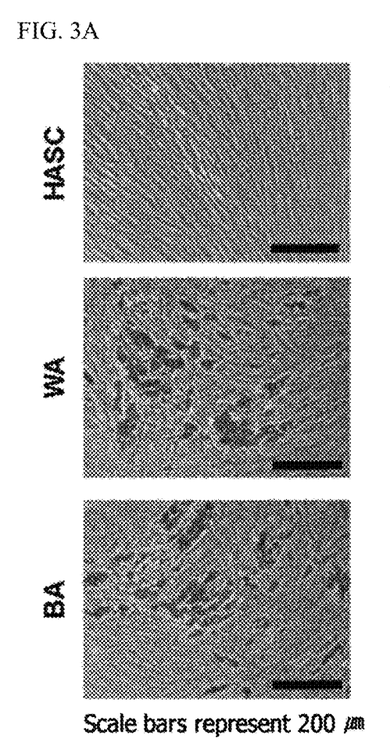
FIGS. 3A-3C shows the ability of differentiation from human adipose-derived stem cells into beige adipocytes [FIG. 3A; human adipose-derived stem cells (HASC), white adipocytes (WA) and beige adipocytes (BA) confirmed through Oil Red O staining, FIG. 3B; the expression of the mRNA of UCP1, the major differentiation factor of beige adipocytes, confirmed through RT-PCR.
Figure 3B:
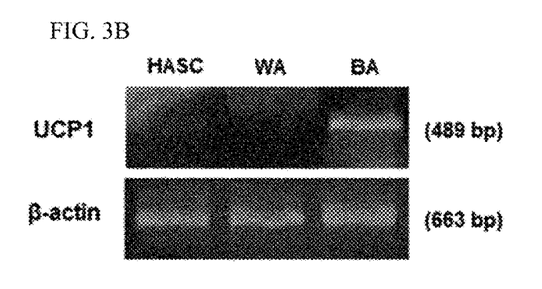
Figure 3C:
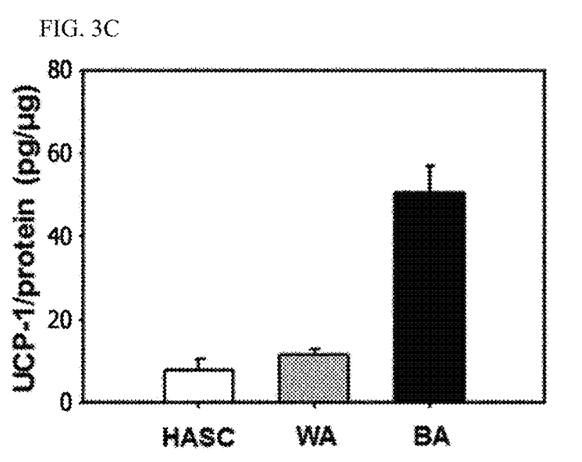

Example 1: Isolation of Exosome From Stem Cells Differentiating Into Beige Adipocytes In order to isolate an exosome from stem cells differentiating into beige adipocytes, human adipose-derived stem cells were cultured to about 80-90% in a normal culture medium (Dulbecco's modified Eagle's medium (DMEM) containing 10% fetal bovine serum and 1% penicillin/streptomycin). Then, after replacing the cell culture medium with a beige adipocyte differentiation medium (high-glucose Dulbecco's modified Eagle's medium containing 5% fetal bovine serum, 1% penicillin/streptomycin, 1 μM dexamethasone, 0.5 mM 3-isobutyl-1-methylxanthine, 10 μg/mL insulin and 2 μM rosiglitazone), the cells were induced to differentiate into beige adipocytes by culturing for 3 weeks. The differentiated cells were stained with Oil Red O and the differentiation into beige adipocytes was confirmed through the expression level of UCP-1 (FIGS. 3A-3C).

Figure 1:
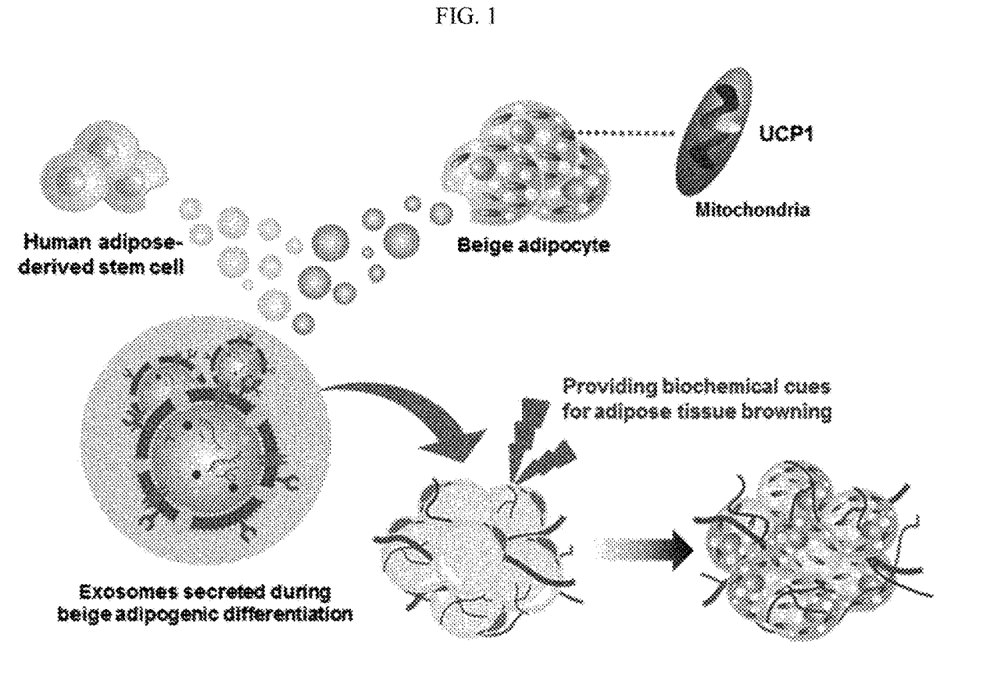
FIG. 1 schematically shows an exosome derived from stem cells differentiating into beige adipocytes and its application.
Figure 2:
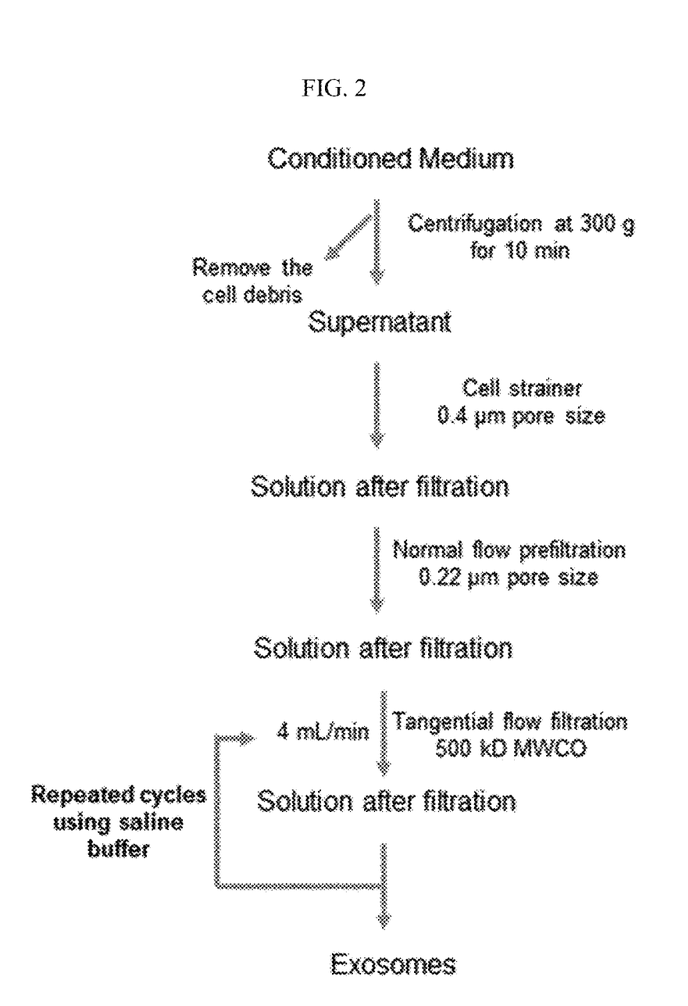
FIG. 2 schematically describes a method for isolating an exosome from stem cells differentiating into beige adipocytes.

In order to isolate an exosome, the stem cells were maintained for 24 hours after replacing the medium with a serum-free medium with no phenol red added and the cell culture supernatant was recovered. The recovered cell culture supernatant was centrifuged at 300×g for 10 minutes to remove the cell residue. Then, a cell strainer with a pore size of 0.4 μm was used to remove the residue greater than the pore size. Then, a filter with a pore size of 0.22 μm was used to remove the cell residue greater than the pore size. The filtered solution was filtered by TFF (tangential flow filtration) using a filter with a MWCO (molecular weight cut-off) of 500 kD at a flow rate of 4 mL/min to remove proteins. After adding a saline buffer to the recovered solution, an exosome was obtained by repeating TFF (FIG. 2).

Example 2: Characterization of Exosome

Figure 4A:
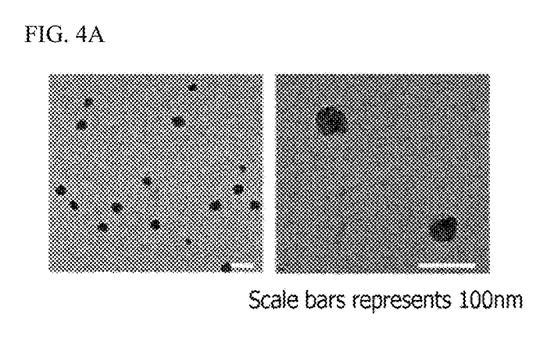
Figure 4B:
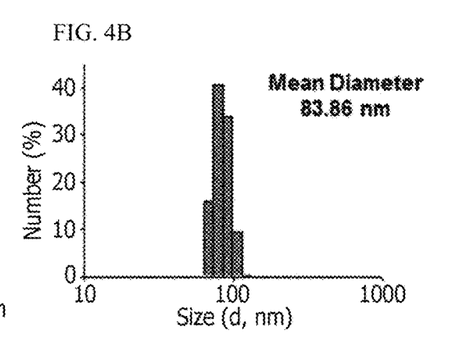
Figure 4C:
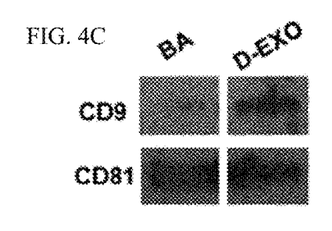
Figure 4D:
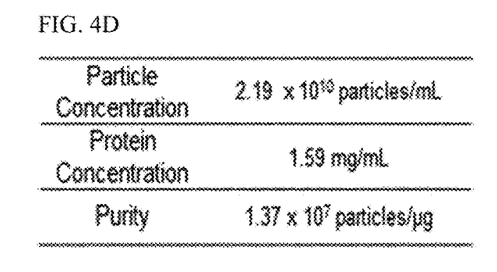

The size and shape of the exosome derived in Example 1 were confirmed by transmission electron microscopy and dynamic light scattering, and the proteins present on the surface of the exosome were confirmed by western blot which detects specific proteins. The purity and yield of the exosome isolated from 400 mL of the cell culture were confirmed by nanoparticle tracking analysis. As a result, the isolated exosome was in the form of round nanoparticles (FIG. 4A) and had an average size of 83.86 nm (FIG. 4B). The expression of the exosome-specific markers CD9 and CD81 on the surface of the exosome membrane was also confirmed (FIG. 4C). The concentration of the exosome isolated using the multi-filter system was $2\times10^{10}$ particles/mL. The protein concentration was 1.59 mg/mL and the purity was $1.37\times10^7$ particles/m.

Example 3: Induction of Differentiation Into Beige Adipocytes Using Exosome Derived From Stem Cells Differentiating Into Beige Adipocytes In order to induce differentiation of stem cells into beige adipocytes, a medium composition containing the exosome derived from stem cells differentiating into beige adipocytes (D-EXO) was used. The medium composition was prepared by adding the exosome at a concentration of $0.5\times10^8$, $1\times10^8$ or $2\times10^8$ particles/mL to a stem cell culture medium. After treating cultured human adipose-derived stem cells with each medium composition, the medium composition was replaced once in every 3 days for 21 days. As a negative control group, stem cells proliferated in a normal culture medium (high-glucose Dulbecco's modified Eagle's medium containing 10% fetal bovine serum and 1% penicillin/streptomycin) were used. As a positive control group, stem cells cultured in a beige adipocyte differentiation medium (DM) containing 5% fetal bovine serum, 1 μM dexamethasone, 10 μg/mL insulin, 0.5 mM 3-isobutyl-methylxanthine and 2 μM rosiglitazone were used. As a comparison group, stem cells treated with an exosome derived from proliferating stem cells (P-EXO) were used. The stem cells induced to differentiate into beige adipocytes for 14 days were stained with Oil Red O to confirm the differentiation into beige adipocytes. Also, the expression of the beige adipocyte marker UCP-1 in the cells was analyzed using a UCP-1 ELISA kit.

Figure 6:
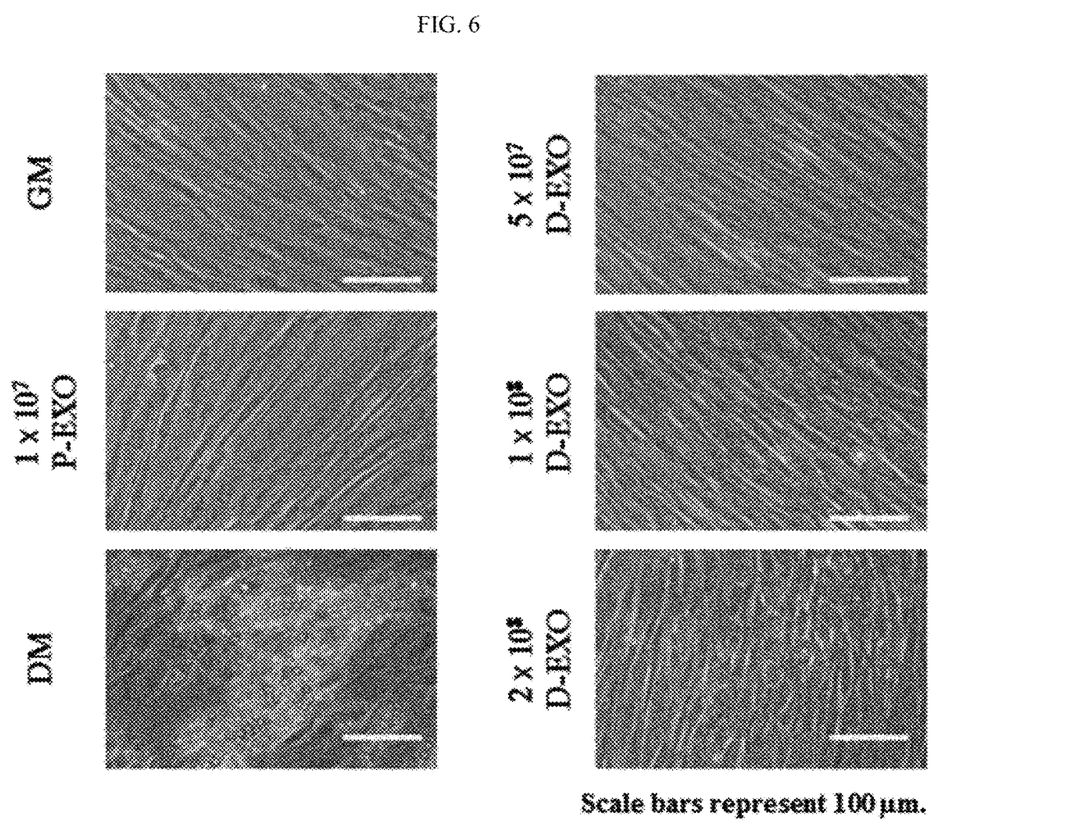
FIG. 6 shows a result of staining human adipose-derived stem cells induced to differentiate into beige adipocytes with Oil Red O [GM: growth medium, negative control group, DM: differentiation medium, positive control group, P-EXO: exosome derived from proliferating stem cells, D-EXO: exosome derived from stem cells differentiating into beige adipocytes].
Figure 7:
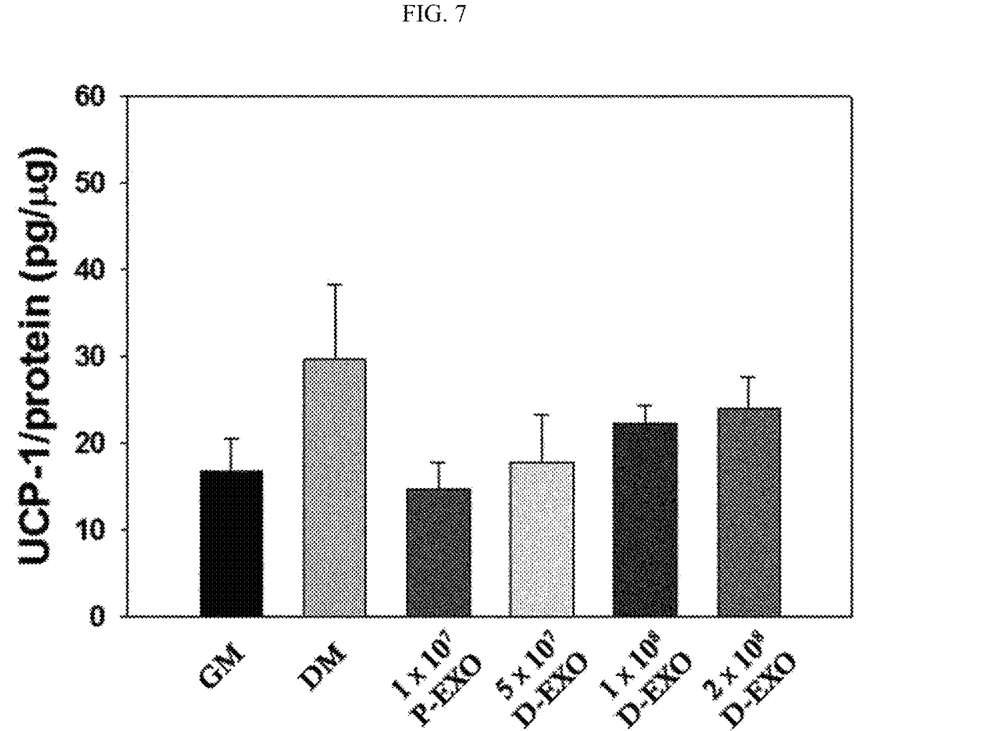
FIG. 7 shows a result of investigating the expression of the UCP-1 protein in human adipose-derived stem cells induced to differentiate into beige adipocytes by ELISA [GM: growth medium, negative control group, DM: differentiation medium, positive control group, P-EXO: exosome derived from proliferating stem cells, D-EXO: exosome derived from stem cells differentiating into beige adipocytes].

After treating with the exosome derived from stem cells differentiating into beige adipocytes (D-EXO) for 14 days, oil was produced similarly to the beige adipocyte differentiation medium (FIG. 6) and the UCP-1 protein was expressed (FIG. 7), suggesting that differentiation into beige adipocytes was induced. It was confirmed that the stem cells treated with the exosome derived from proliferating stem cells (P-EXO) proliferated only without differentiating into adipocytes.

Example 4: Cellular Uptake of Exosome

Figure 5:
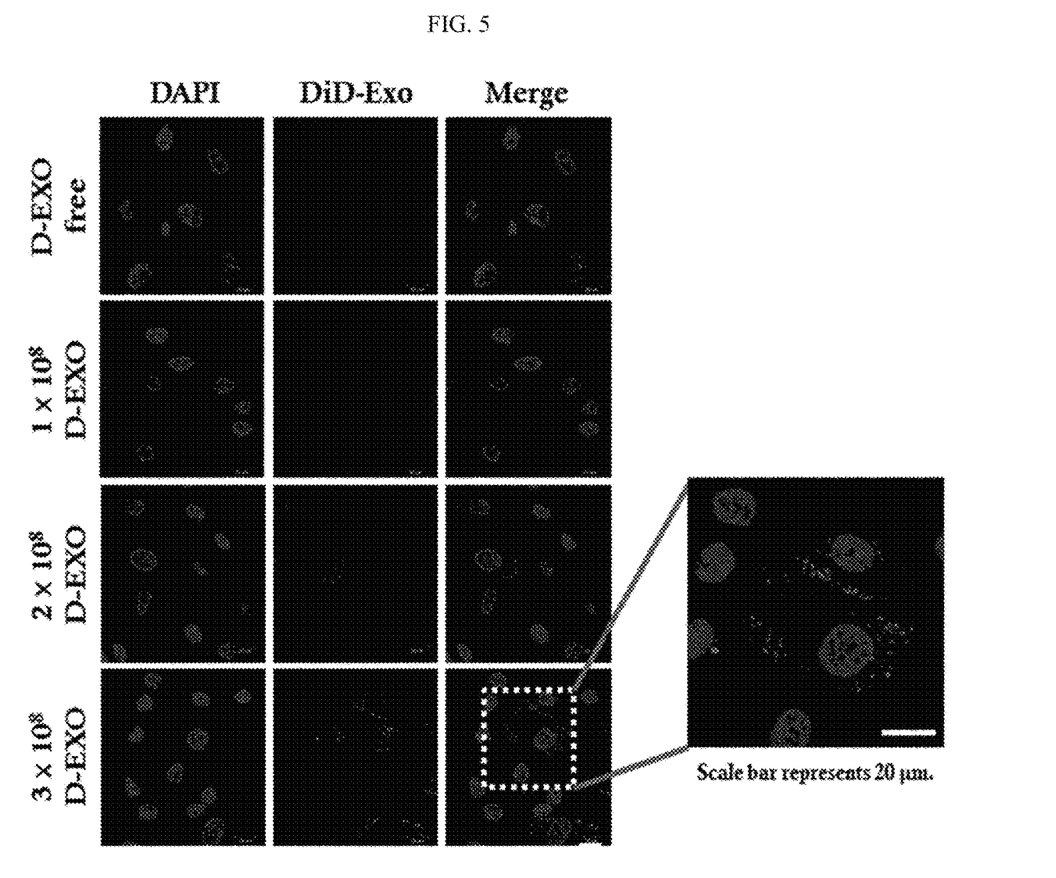
FIG. 5 shows a result of investigating the degree of absorption of an isolated exosome into human adipose-derived stem cells by confocal fluorescence microscopy [D-EXO: exosome derived from stem cells differentiating into beige adipocytes].

In order to investigate the degree of uptake of the exosome into cells, a medium composition containing the exosome derived from stem cells differentiating into beige adipocytes (D-EXO) was used. The exosome was mixed with a fluorescent stain (DiD) for 15 minutes at 37° C. in order to label the surface of the exosome. Then, the unreacted stain was removed using an exosome spin column. After treating human adipose-derived stem cells with the fluorescence-labeled exosome at a concentration of $1\times10^8$, $2\times10^8$ or $3\times10^8$ particles/mL and culturing for 1 hour, the nuclei of the stem cells were stained with DAPI and the cells were observed using a confocal laser scanning microscope. The cellular uptake was in proportional to the exosome concentration. It was also confirmed that a large quantity of the exosome was transferred not only to the cytoplasm but also to the nuclei of the stem cells within 1 hour after treatment with the exosome (FIG. 5).

Example 5: Obesity-Treating Effect in ob/ob Mouse

In order to investigate the obesity-treating effect of the exosome, the exosome was intraperitoneally injected to C57BL6/J-ob/ob mouse. 6-week-old mice were accustomed for 1 week and the exosome derived from proliferating stem cells (P-EXO) and the exosome derived from stem cells differentiating into beige adipocytes (D-EXO) were administered for 2 weeks, respectively. Then, the change in body weight for 4 weeks was measured.

Figure 8:
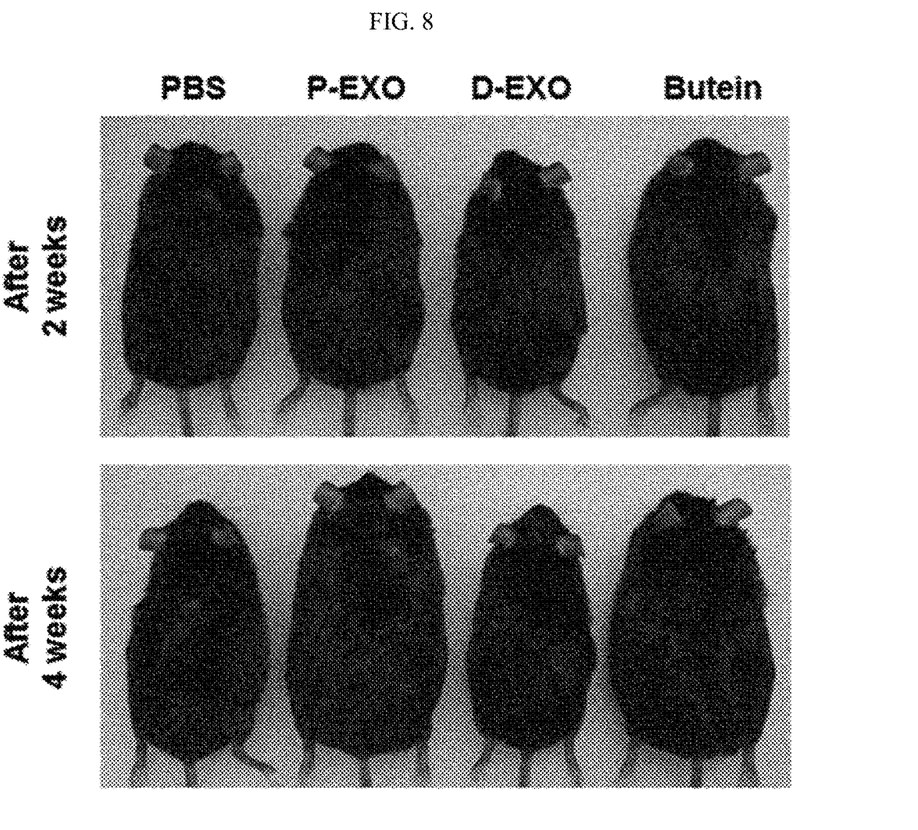
FIG. 8 shows the change in appearance of the obesity animal model C57BL6/J-ob/ob mouse administered with D-EXO for 4 weeks [PBS: control group administered with phosphate buffer saline (N=3), P-EXO: control group intraperitoneally administered with $3\times10^8$ P-EXO particles with two-day intervals (N=3), D-EXO: group intraperitoneally administered with $3\times10^8$ D-EXO particles with two-day intervals (N=3), Butein: group intraperitoneally administered with 15 mg/kg butein with two-day intervals (N=3)].
Figure 9:
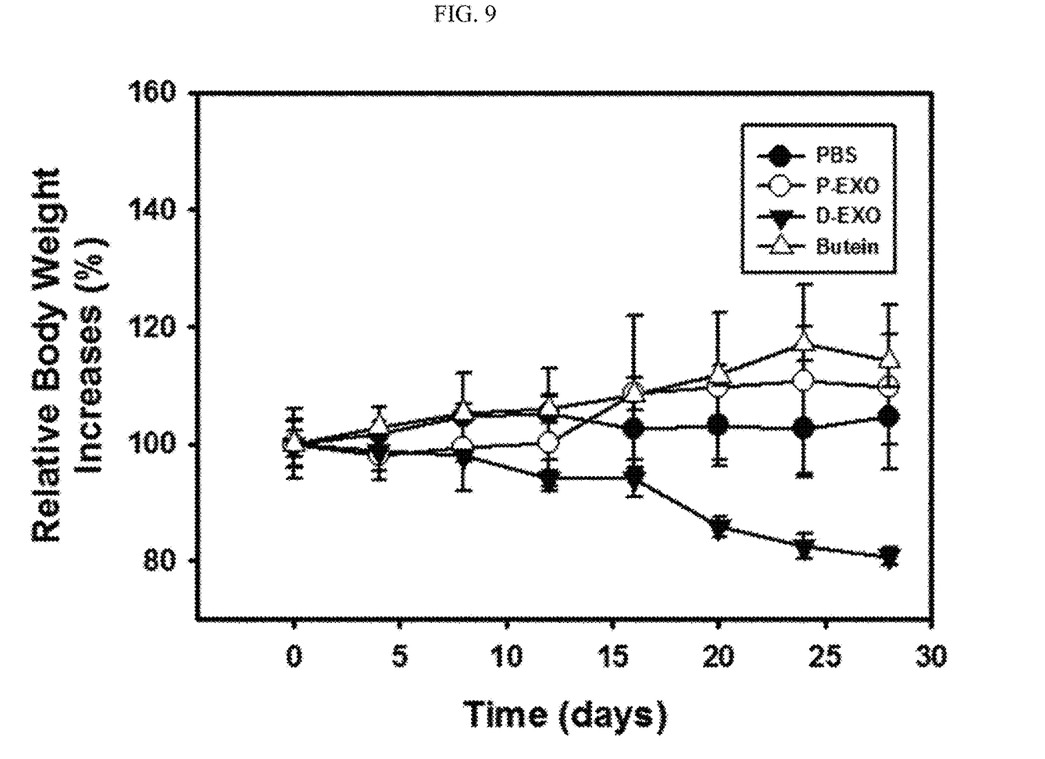
FIG. 9 shows the change in body weight of the obesity animal model C57BL6/J-ob/ob mouse intraperitoneally administered with PBS, P-EXO, D-EXO or butein for 2 weeks with two-day intervals [PBS: control group administered with phosphate buffer saline (N=3), P-EXO: control group intraperitoneally administered with $3\times10^8$ P-EXO particles with two-day intervals (N=3), D-EXO: group intraperitoneally administered with $3\times10^8$ D-EXO particles with two-day intervals (N=3), Butein: group intraperitoneally administered with 15 mg/kg butein with two-day intervals (N=3)].

Specifically, the exosome was dispersed in PBS at a concentration of $3\times10^9$ particles/mL. Then, after intraperitoneally injecting the exosome to C57BL6/J-ob/ob mouse, the change in body weight for 4 weeks was measured. As a negative control group, PBS not containing the exosome was used. As a positive control group, a solution containing butein, which is known to be effective in preventing obesity, was used. 4 weeks later, the change in appearance and body weight was observed to evaluate the obesity-treating effect. As a result, it was confirmed that the body weight of the animal treated with the exosome derived from stem cells differentiating into beige adipocytes (D-EXO) was decreased (FIG. 8 and FIG. 9).

Example 6: Diabetes-Treating Effect in ob/ob Mouse

Figure 10:
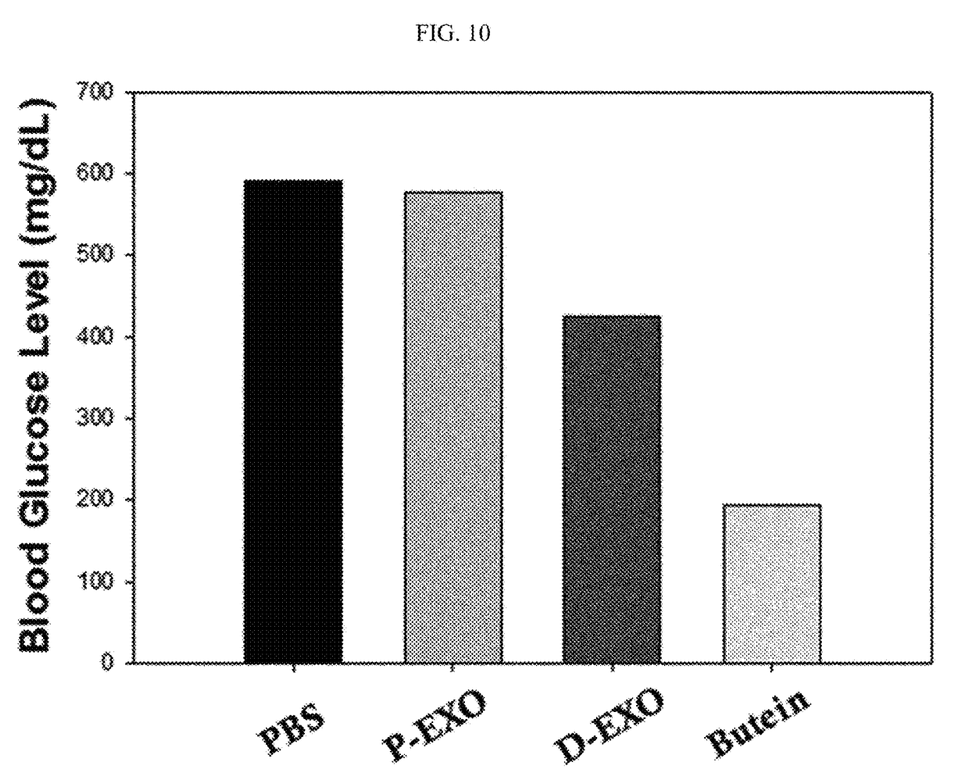
FIG. 10 shows the blood glucose level of the obesity animal model C57BL6/J-ob/ob mouse intraperitoneally administered with PBS, P-EXO, D-EXO or butein for 2 weeks with two-day intervals [PBS: control group administered with phosphate buffer saline (N=3), P-EXO: control group intraperitoneally administered with $3\times10^8$ P-EXO particles with two-day intervals (N=3), D-EXO: group intraperitoneally administered with $3\times10^8$ D-EXO particles with two-day intervals (N=3), Butein: group intraperitoneally administered with 15 mg/kg butein with two-day intervals (N=3)].

In order to investigate the diabetes-treating effect of the exosome, the exosome was intraperitoneally injected to C57BL6/J-ob/ob mouse. 6-week-old mice were accustomed for 1 week and the exosome derived from proliferating stem cells (P-EXO) and the exosome derived from stem cells differentiating into beige adipocytes (D-EXO) were administered for 2 weeks, respectively. Then, blood glucose level was measured after fasting for 12 hours. It was confirmed that the mouse administered with the exosome derived from stem cells differentiating into beige adipocytes (D-EXO) showed decreased blood glucose level as compared to the mouse treated with PBS or P-EXO (FIG. 10).

What is claimed is:

1. A method of inducing differentiation of human stem cells into beige adipocytes, comprising a step of contacting the human stem cells with isolated exosomes as an active ingredient, wherein said exosomes have been previously produced and released in the process of differentiating human adipose-derived stem cells into beige adipocytes by culturing human adipose-derived stem cells with a beige adipocyte differentiation medium, wherein said isolated exosomes express CD9 and CD81 and have a diameter from about 50 to 150 nm in size.

2. The method according to claim 1, wherein human stem cells differentiating into beige adipocytes are bone marrow stem cells, umbilical cord stem cells or adipose-derived stem cells.

3. The method according to claim 1, wherein the composition exosomes are comprised in a pharmaceutical composition.

4. The method according to claim 3, wherein the pharmaceutical composition is for treating or preventing a metabolic disease.

5. The method according to claim 4, wherein the metabolic disease is obesity or diabetes.

6. The method according to claim 1, wherein the exosomes are comprised in a food composition.

7. The method according to claim 6, wherein the food composition is for improving or preventing obesity or diabetes.

8. The method according to claim 1, wherein the exosomes are comprised in a medium composition.

9. The method according to claim 1, wherein the human stem cells to be treated with the exosomes are present in a human subject having a metabolic disease, and the step of contacting stem cells with the exosomes is carried out by administering the exosomes to the subject.

10. The method according to claim 9, wherein the metabolic disease of the subject is improved or treated by the administration of the exosomes.

11. The method according to claim 10, wherein the metabolic disease is obesity or diabetes.

* * * * *